(12) United States Patent
Beyens

(10) Patent No.: US 9,360,399 B2
(45) Date of Patent: Jun. 7, 2016

(54) MEASURING PROBE FOR MEASUREMENTS IN MOLTEN METAL OR SLAG

(71) Applicant: Heraeus Electro-Nite International N.V., Houthalen (BE)

(72) Inventor: Dries Beyens, Kinrooi (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 420 days.

(21) Appl. No.: 14/065,909

(22) Filed: Oct. 29, 2013

(65) Prior Publication Data
US 2014/0119404 A1 May 1, 2014

(30) Foreign Application Priority Data
Oct. 31, 2012 (DE) .......................... 10 2012 021 338

(51) Int. Cl.
| | | |
|---|---|---|
| *G01K 1/08* | (2006.01) | |
| *G01K 1/10* | (2006.01) | |
| *G01K 1/12* | (2006.01) | |
| *G01K 1/14* | (2006.01) | |
| *G01K 7/02* | (2006.01) | |
| *G01N 1/12* | (2006.01) | |

(Continued)

(52) U.S. Cl.
CPC .............. *G01N 1/125* (2013.01); *G01N 27/411* (2013.01); *G01N 33/206* (2013.01)

(58) Field of Classification Search
CPC ............. G01K 1/18; G01K 1/10; G01K 1/12; G01K 1/14; G01K 13/00; G01K 7/00
USPC ........... 374/16, 100, 139, 140, 141, 142, 179, 374/163, 208; 136/324; 73/866.5
See application file for complete search history.

(56) References Cited

U.S. PATENT DOCUMENTS 3,773,641 A * 11/1973 Fitterer .............. G01N 27/4118
204/423
4,881,824 A * 11/1989 Falk ........................ G01N 1/125
136/234

(Continued)

FOREIGN PATENT DOCUMENTS

| | | | |
|---|---|---|---|
| DE | 10 2005 060 493 B3 | 11/2006 | |
| DE | 10 2005 060 492 B3 | 5/2007 | |

(Continued)

OTHER PUBLICATIONS

English translation of an Office Action issued Aug. 19, 2014 in JP Application No. 2013-225796.

*Primary Examiner* — Gail Kaplan Verbitsky
(74) *Attorney, Agent, or Firm* — Panitch Schwarze Belisario & Nadel LLP

(57) ABSTRACT

A measuring probe is provided for taking measurements in molten metal or slag, the probe including a measuring head having an immersion end and a rear end. At least one electrochemical sensor, one thermocouple, and one bath contact of the electrochemical sensor are arranged at the immersion end, and the thermocouple and electrochemical sensor each protrude from the immersion end adjacent to each other. The bath contact is formed from a strip of metal arranged around and between the thermocouple and the electrochemical sensor in appropriate manner, such that two chambers are formed that are open at the immersion end. The thermocouple is arranged in one chamber and the electrochemical sensor is arranged in the other chamber and both are held by fixation material.

6 Claims, 3 Drawing Sheets

(51) Int. Cl.
  *G01N 27/411* (2006.01)
  *G01N 33/20* (2006.01)

(56) References Cited

U.S. PATENT DOCUMENTS

| | | | | |
|---|---|---|---|---|
| 4,896,549 A | * | 1/1990 | Falk | G01N 1/125 374/140 |
| 4,964,736 A | * | 10/1990 | Cure | G01N 33/206 136/234 |
| 5,415,052 A | * | 5/1995 | Baerts | G01N 1/125 73/864.51 |
| 7,434,470 B2 | * | 10/2008 | Engelhardt | G01D 11/245 374/E13.006 |
| 7,998,399 B2 | * | 8/2011 | Dams | G01N 33/206 266/78 |
| 2007/0137286 A1 | | 6/2007 | Neyens | |

FOREIGN PATENT DOCUMENTS

| | | |
|---|---|---|
| DE | 10 2010 024 282 A1 | 12/2011 |
| JP | S54-17791 U | 2/1979 |
| JP | S61-82266 U | 5/1986 |
| JP | H07-63620 A | 3/1995 |
| JP | 2000-249680 A | 9/2000 |
| JP | 2003-207473 A | 7/2003 |
| JP | 2007-163494 A | 6/2007 |

\* cited by examiner

MEASURING PROBE FOR MEASUREMENTS IN MOLTEN METAL OR SLAG

BACKGROUND OF THE INVENTION

The invention relates to a measuring probe for measurements in molten metal or slag, the probe having a measuring head comprising an immersion end and a rear end, wherein at least one electrochemical sensor, one thermocouple, and one bath contact of the electrochemical sensor are arranged at the immersion end.

Measuring probes of this type are known, for example, from German Patent DE 10 2005 060 492 B3. This document discloses multiple measuring probes and an inlet opening for a sample chamber at the immersion end of a measuring head, wherein each sensor comprises contact elements at the side of the measuring head facing away from the immersion end. The sensors are affixed with cement inside the measuring head. A similar measuring probe is known from German Patent DE 10 2005 060 493 B3. Aside from multiple sensors and an inlet opening in a sample chamber, a bath contact is disclosed at the immersion side of the measuring head disclosed herein. Similar samplers are also known from German published patent application DE 10 2010 024 282 A1.

BRIEF SUMMARY OF THE INVENTION

It is the object of the present invention to improve on the known measuring probes. The object is met by embodiments of the invention described and claimed in the following.

By having one thermocouple and one electrochemical sensor each protrude from the immersion end adjacent to each other, by providing the bath contact from a strip of metal that is arranged around the thermocouple and the electrochemical sensor and between the thermocouple and the electrochemical sensor in appropriate manner, such that two chambers are formed that are open at the immersion end, wherein the thermocouple is arranged in one chamber and the electrochemical sensor is arranged in the other chamber and each is held by fixation material, it is feasible to affix the sensors optimally and adapted to the specific sensor type and to thus increase the measuring accuracy thereof. In this context, an arrangement adjacent to each other shall be understood to mean that a thermocouple and an electrochemical sensor are arranged next to each other and essentially parallel to each other, such that no further sensor is arranged directly between the thermocouple and the electrochemical sensor.

The electrochemical sensor can, in particular, be a solid electrolyte-based oxygen sensor. The bath contact is arranged to be approximately parallel to the longitudinal axes of the thermocouple and the electrochemical sensor, such that it surrounds the lateral surfaces of the two components and is arranged essentially parallel to these in the measuring head. Thus, it forms, as seen in the immersion direction of the measuring probe, a closed line around the two parts (thermocouple and electrochemical sensor) which, in addition, fully divides the surface thus formed, such that two approximately equal surfaces are produced, in which the thermocouple and/or the electrochemical sensor are respectively arranged. The two chambers thus formed are closed by the bath contact only on the side, but not on their immersion end and at the opposite side facing away from the immersion end.

Preferably, the fixation material used for the thermocouple is different from the fixation material used for the electrochemical sensor. This allows for specific adaptation and optimization of the fixation material for the part affixed by it. In particular, the fixation material for the thermocouple can be formed by generally known refractory cement, and the fixation material for the electrochemical sensor can be formed by generally known foundry sand or molding sand. In this type of arrangement, on the one hand, the refractory cement optimally protects the cold soldering site of the thermocouple, whereas the gas-permeable foundry sand or molding sand is optimal for the interaction of bath contact and electrochemical sensor and transports away gases that are generated. Also, a layer of refractory cement (in particular approx. 0.5 cm in thickness) can be arranged in the chamber for the electrochemical sensor on the side facing away from the immersion end, below the foundry sand or molding sand, i.e. approx. at the foot of the sensor, since this allows the fixation of the sensor to be strengthened further.

Preferably, the measuring probe is characterized in that the chambers formed through the bath contact comprise, at their side facing away from the immersion end, a preferably common connector element with electrical connectors for the thermocouple, the electrochemical sensor, and the bath contact itself. A connector element in this sense is a contact site for connecting the electrical connectors of the sensors and/or of the bath contact to signal cables for further conductance. The connectors protruding from the connector element can be provided as plug-in contacts.

Preferably, the chambers and the connector element are designed as a uniform module that is provided to be self-supporting. This allows the sensor unit made up of thermocouple, electrochemical sensor, and bath contact to be manufactured separately, without attendant problems and in simple manner, whereby the module can then be inserted into the measuring head of the measuring probe. Electrical connection by means of plug-in contacts of the connector element is preferred for this purpose.

Expediently, a sample chamber can be additionally arranged on the measuring head, wherein an inlet opening of the inlet channel of the sample chamber protrudes from the immersion end of the measuring head.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1A:
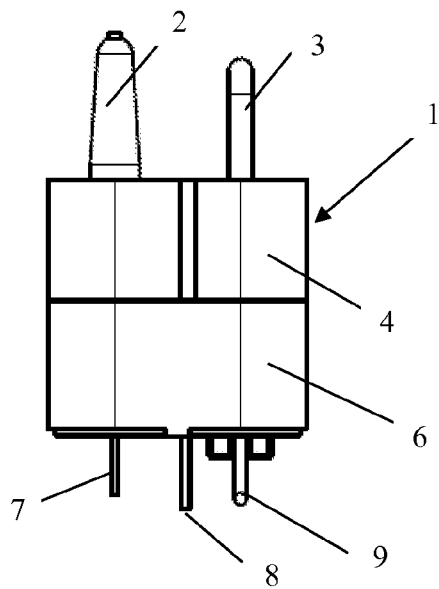
FIGS. 1*a*, 1*b* and 1*c* are respectively side, perspective and top end views of a module, made up of a thermocouple, an electrochemical sensor, a bath contact, and a connector element, useful in one embodiment of a measuring head according to the invention.

The module 1 shown in FIG. 1 comprises an oxygen sensor 2 as the electrochemical sensor and a thermocouple 3. The longitudinal axes of each are oriented approximately parallel to each other. They are surrounded by bath contact 4 approximately parallel to their longitudinal axes, wherein the bath contact 4 surrounds both sensors together and also forms a boundary layer 5 between them, such that one chamber each is formed for the thermocouple 3 and the oxygen sensor 2, respectively. In this context, the tips of the thermocouple 3 and of the oxygen sensor 2 protrude from the respective chambers at the immersion end of the module 1. On the opposite end, facing away from the immersion end, there is a connector element 6 adjacent to the bath contact 4, wherein the connector contacts (7 for the oxygen sensor 2, 8 for the bath contact 4, and 9 for the thermocouple 3) are arranged toward the end thereof that faces away from the immersion end. The connector contacts 7, 8, 9 are needed to conduct electrical signals further.

Foundry sand or molding sand 10 affixing the oxygen probe 2 in the module 1 is arranged between the bath contact 4 and the oxygen sensor 2. The thermocouple 3 is affixed in the module 1 by refractory cement 11. The refractory cement 11 is arranged between the bath contact 4 and the thermocouple 3.

Figure 1B:
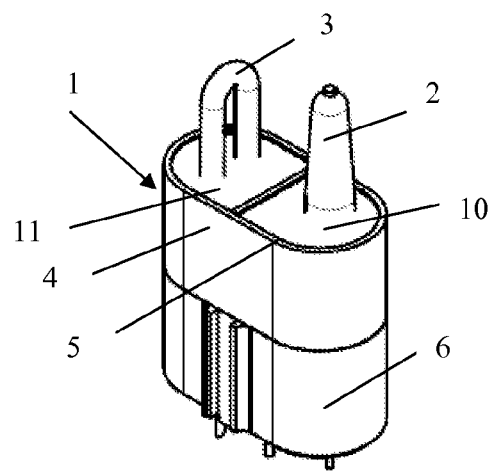
Figure 1C:
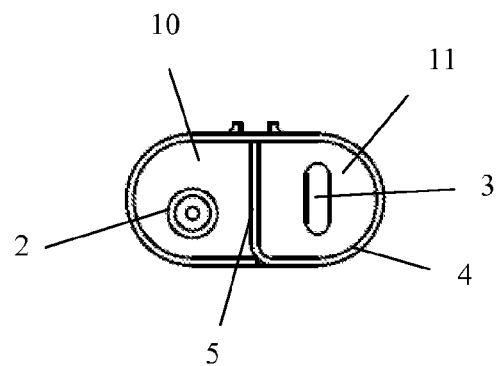

Module 1 is shown in a side view in FIG. 1*a* such that the protruding sensors 2, 3 at the immersion end and the connector contacts 7, 8, 9 at the end facing away from the immersion end are recognizable. FIG. 1*b* shows a perspective view of the module 1, and FIG. 1*c* shows a top view seen from the immersion end. A module 1 of this type can be manufactured separately. This means that thermocouple 3, oxygen sensor 2, and bath contact 4 can be positioned in the requisite orientation with respect to each other and can be fixed with respect to each other using cement 11 and/or foundry sand 10. This arrangement is bounded at its rear end by the connector element 6, which accommodates the connector contacts 7, 8, 9. A module of this type can be manufactured inexpensively and can then be inserted into a corresponding recess of a measuring probe.

Figure 2:
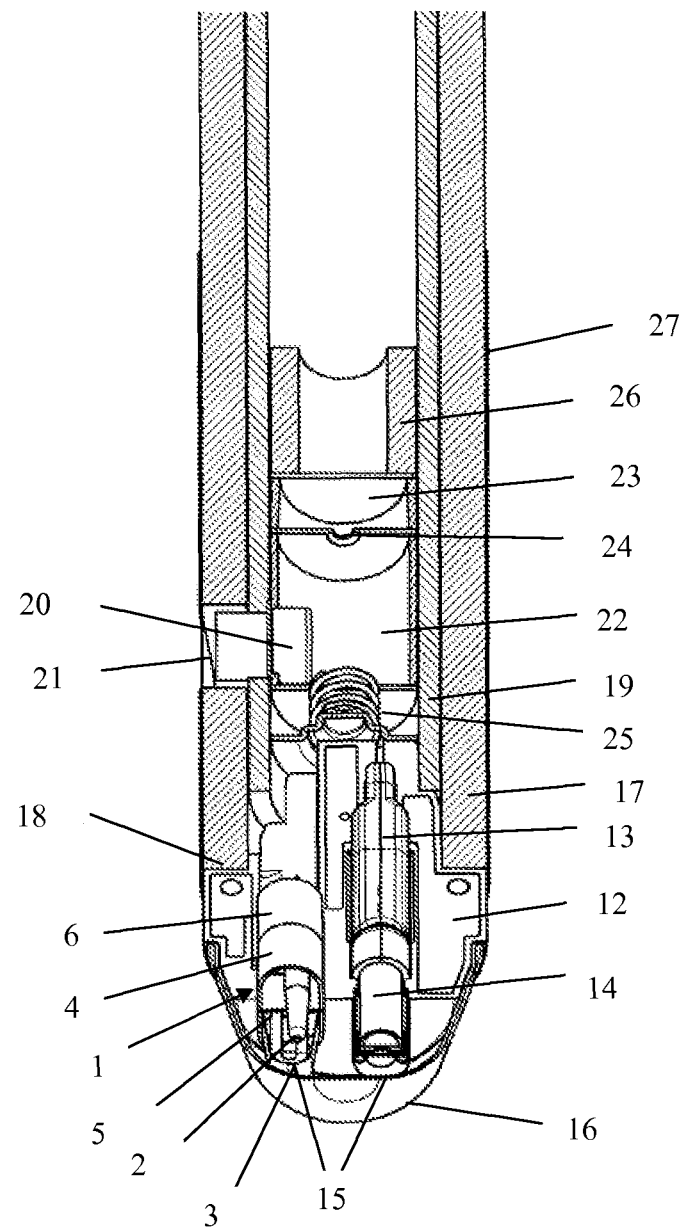
FIG. 2 is a schematic, longitudinal perspective, sectional view of a measuring probe according to an embodiment of the invention and containing a module according to FIG. 1.

A measuring probe of this type is shown in exemplary manner in FIG. 2. Aside from the module 1, the Figure shows a sample chamber 13 to be arranged on the measuring head 12 formed from foundry sand. The sample chamber 13 comprises an inlet tube 14 made of quartz glass, whose inlet opening protrudes from the immersion end of the measuring head 12. The inlet opening of the inlet tube 14, as well as the thermocouple 3 and the oxygen sensor 2 of the module 1, are covered by conventional protective caps 15, which melt and/or dissolve during the use of the measuring probe in molten steel and thus enable the measurement or sampling. The entire immersion end of the measuring head 12 is surrounded by a slag cap 16, which is also known and protects the measuring head from damage during transport and while it is pushed through the slag layer on molten steel.

The measuring head 12 is affixed in a support tube 17 made of cardboard by means of a refractory adhesive 18. A fixation tube 19 made of cardboard, inside of which another sampler is arranged, is arranged inside the support tube 17 in the example shown. This sampler comprises an inlet opening, which is guided laterally through the support tube 17 and has an inlet channel 20 made of quartz glass. The inlet channel 20 is closed on its outside by a paper cap 21 that dissolves when the support tube penetrates into a slag layer. Subsequently, slag penetrates into a pre-chamber 22 and then into the slag sample chamber 23 arranged above the pre-chamber. Pre-chamber 22 and slag sample chamber 23 are surrounded by metal walls on all sides. The inlet opening 24 into the slag sample chamber is arranged in centric position. A helical spring 25 can be arranged for fixation purposes between the pre-chamber 22 and the rear side of the measuring head 12, which is arranged upstream of it, as seen in the immersion direction. The end of the slag sample chamber 23 facing away from the immersion end is affixed through yet another cardboard tube 26.

A so-called splash protection layer 27 made of metal is arranged at the external circumference of the support tube 17. The purpose of the splash protection layer 27 is to prevent the cardboard from burning and/or dissolving immediately upon the support tube 17 being immersed into the slag layer and/or molten steel, whereby gases and interfering particles would be released that may interfere with the measurements and/or sampling processes.

Figure 3:
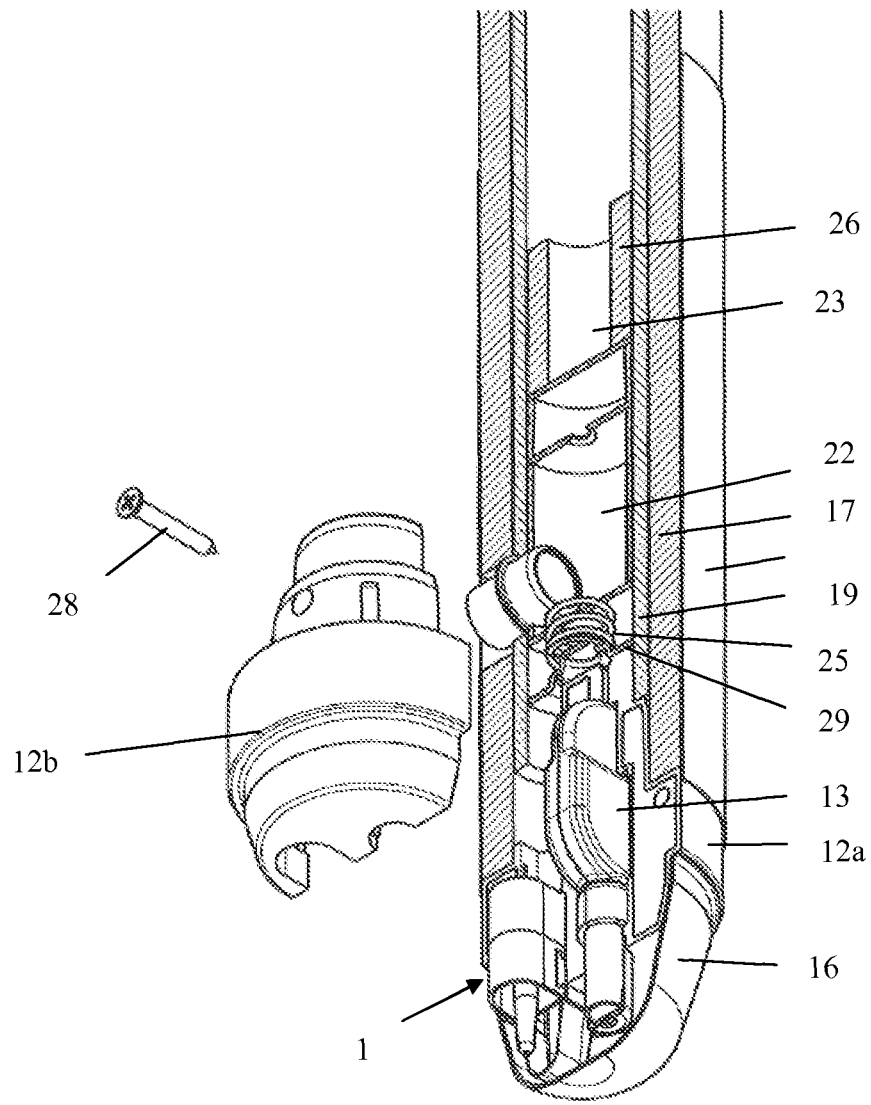
FIG. 3 is a schematic, exploded, sectional view of a measuring head according to an embodiment of the invention.

FIG. 3 shows the assembly process of the measuring head 12. The measuring head 12 is initially divided into two parts 12*a* and 12*b* and is pressed from foundry sand. It contains corresponding recesses for accommodation of the sample chamber 13 and module 1. Module 1 and sample chamber 13 are inserted into the recesses, and then the measuring head is completed by attaching the second part 12*b*. The two parts 12*a* and 12*b* of the measuring head 12 are affixed to each other by means of a screw 28. After this, follows the assembly to the support tube and the parts arranged on it earlier, such as the slag sample chamber 23 and its pre-chamber 22. The helical spring 25 is affixed to the side of the measuring head 12 facing away from the immersion end by a steel plate 29, which closes the measuring head with respect to the pre-chamber 22 of the slag sample chamber 23.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A measuring probe for taking measurements in molten metal or slag, the probe comprising a measuring head having an immersion end and a rear end, an electrochemical sensor, a thermocouple, and a bath contact of the electrochemical sensor being arranged at the immersion end, wherein the thermocouple and electrochemical sensor each protrude from the immersion end adjacent to each other, the bath contact comprising a strip of metal arranged around and between the thermocouple and the electrochemical sensor in a manner such that two chambers are formed being open at the immersion end, and wherein the thermocouple is arranged in one of the chambers and the electrochemical sensor is arranged in another of the chambers and both the thermocouple and the electrochemical sensor are held by fixation material.

2. The measuring probe according to claim 1, wherein the fixation material used for the thermocouple is different from the fixation material used for the electrochemical sensor.

3. The measuring probe according to claim 2, wherein the fixation material used for the thermocouple is refractory cement and the fixation material used for the electrochemical sensor is foundry sand.

4. The measuring probe according to claim 1, wherein the chambers formed by the bath contact comprise, at their end facing away from the immersion end, a common connector element having electrical connectors for the thermocouple, the electrochemical sensor, and the bath contact.

5. The measuring probe according to claim 4, wherein the chambers and the connector element form a module which is provided to be self-supporting.

6. The measuring probe according to claim 1, further comprising a sample chamber arranged on the measuring head, wherein an inlet opening of the inlet channel of the sample chamber protrudes from the immersion end of the measuring head.

* * * * *